United States Patent
Taylor

(10) Patent No.: US 12,020,781 B1
(45) Date of Patent: Jun. 25, 2024

(54) SEARCHING OF CHEMICAL STRUCTURES

(71) Applicant: Benchling, Inc., San Francisco, CA (US)

(72) Inventor: Lawrence Taylor, San Francisco, CA (US)

(73) Assignee: Benchling, Inc., San Francisco, CA (US)

( * ) Notice: Subject to any disclaimer, the term of this patent is extended or adjusted under 35 U.S.C. 154(b) by 0 days.

(21) Appl. No.: 18/233,726

(22) Filed: Aug. 14, 2023

(51) Int. Cl.
| | |
|---|---|
| *G01N 33/48* | (2006.01) |
| *G01N 33/50* | (2006.01) |
| *G16C 20/40* | (2019.01) |
| *G16C 20/80* | (2019.01) |
| *G16C 20/90* | (2019.01) |
| *G16C 60/00* | (2019.01) |

(52) U.S. Cl.
CPC ............. *G16C 20/40* (2019.02); *G16C 20/80* (2019.02); *G16C 20/90* (2019.02); *G16C 60/00* (2019.02)

(58) Field of Classification Search
CPC ........ G16C 20/40; G16C 20/80; G16C 20/90; G16C 60/00
See application file for complete search history.

(56) References Cited

PUBLICATIONS

Yang et al. Concepts and applications of chemical fingerprint for hit and lead screening. Drug Discovery Today, vol. 27, Nov. 2022, pp. 1-16.*
Kausar et al. Analysis and comparison of vector space and metric space representations in QSAR modeling, vol. 24, article 1698, 22 pages. (Year: 2019).*
Thiel et al. Blocked inverted indices for exact clustering of large chemical spaces. Journal of Chemical Information and Modeling, vol. 54, pp. 2395-2401. (Year: 2014).*
Aung et al., "An Indexing Scheme for Fast and Accurate Chemical Fingerprint Database Searching," Chemical Database Searching, 2010, pp. 288-305.
Broder et al., "Efficient Query Evaluation using a Two-Level Retrieval Process," Presented at CIKM'03, Nov. 3-8, 2003, New Orleans, Louisiana, USA, 9 pages.
Ding et al., "Faster Top-k Document Retrieval Using Block-Max Indexes," Presented at SIGIR'11, Jul. 24-28, 2011, Beijing, China, 10 pages.

(Continued)

*Primary Examiner* — Russell S Negin
(74) *Attorney, Agent, or Firm* — Fish & Richardson P.C.

(57) ABSTRACT

Methods, systems, and apparatus, including computer programs encoded on computer storage media, for searching chemical structures. One of the methods includes receiving a fingerprint map for each chemical structure of a collection of chemical structures, generating an inverted index for the collection of chemical structures, receiving a request to search the inverted index for matching chemical structures, obtaining a query fingerprint for the query structure, computing a minimum number of bits and a maximum number of bits that must be present in respective fingerprints of candidate structures in the collection of chemical structures in order for a candidate structure to be considered a match for the query structure, and traversing the inverted index to identify candidate structures having fingerprints with a number of bits in between the minimum number of bits and the maximum number of bits.

16 Claims, 8 Drawing Sheets

(56) References Cited

PUBLICATIONS

Kratochvil et al., "Sachem: a chemical cartridge for high-performance substructure search," Journal of Cheminformatics, May 23, 2018, 11 pages.

Nasr et al., "Speeding Up Chemical Searches Using the Inverted Index: The Convergence of Chemoinformatics and Text Search Methods, " J. Chem. Inf. Model., 2012, 52(4):891-900.

Swamidass et al., "Bounds and Algorithms for Fast Exact Searches of Chemical Fingerprints in Linear and Sublinear Time," J. Chem. Inf. Model., 2007, pp. 302-317.

* cited by examiner

SEARCHING OF CHEMICAL STRUCTURES

BACKGROUND

This specification relates to the searching of chemical structures.

A chemical structure refers to a substance composed of one or more atoms, along with any bonds between those atoms. For example, a chemical structure can be a molecule or a compound that includes multiple molecules. Data representing chemical structures can be electronically stored in a database. However, due to the complexity of typical chemical structure queries, querying such databases is typically very slow and difficult to scale. For example, a researcher may want to identify structures in a database that contain another structure as a sub-structure. This may require performing an atom-by-atom comparison, which can include a computationally expensive graph algorithm that is impractical to execute for every structure in the database.

One of the major challenges in conventional searches of chemical structures is quickly identifying candidate structures without iterating over every structure in the database, which typical database indexes are not well suited for. A major limitation with many of these conventional databases is the inability to support queries that combine chemical structure queries with traditional database query predicates, such as queries over metadata fields, text search, etc. Other conventional solutions such as extensions to relational databases are inefficient and difficult to scale.

SUMMARY

This specification describes a cheminformatics platform implemented as computer programs on one or more computers in one or more locations that can query a collection of chemical structures in a way that is fast and horizontally scalable. In addition, the architecture allows the chemical structure queries to be composed with other search engine queries. To do so, the platform can compute structure fingerprints and then index the structures by treating the bits of the structure fingerprint as inverted index terms. In other words, the platform can generate an index having posting lists that each correspond to a bit in the structure fingerprint. This approach allows structures having fingerprints that match a given fingerprint bit to be identified quickly, and in a way that is naturally horizontally scalable. The platform can then provide specialized algorithms built on top of the inverted index that allows users, e.g., researchers, to perform highly sophisticated similarity and sub-structure searches very quickly on entire structure databases of unbounded size.

The cheminformatics platform can be a distributed cloud-based computing system where multiple users and laboratories can upload and store data defining chemical structures. The data can specify one or more features of each chemical structure. For example, the data can include a fingerprint map for each chemical structure that represents various features of a chemical structure. For each structure, the database can store the structure itself, a generated fingerprint, and/or any additional properties or metadata associated with the structure.

The cheminformatics platform can process data defining chemical structures and allow a user to search for a chemical structure in the collection of chemical structures that has similar features or sub-structure as a query structure.

According to a first aspect, there is provided a computer-implemented method that includes receiving a fingerprint map for each chemical structure of a collection of chemical structures, wherein each fingerprint map comprises a plurality of bit terms, wherein each bit term of the plurality of bits represents a different respective feature of a plurality of features of the chemical structure, generating an inverted index for the collection of chemical structures, wherein the inverted index includes a plurality of bit term posting lists, each bit term posting list corresponding to one of the bit terms, and wherein each bit term posting list is associated with all structures in the collection of chemical structures having a feature corresponding to the respective bit term of the bit term posting list, receiving a request to search the inverted index for matching chemical structures, wherein the request specifies a query structure representing a chemical structure comprising one or more molecules, obtaining a query fingerprint for the query structure, wherein the query fingerprint comprises a bit vector comprising bit terms representing which of the plurality of features are present in the query structure, computing, based on the query fingerprint and a target score threshold, a minimum number of bits that must be present in respective fingerprints of candidate structures in the collection of chemical structures in order for a candidate structure to be considered a match for the query structure, computing, based on the query fingerprint and the target score threshold, a maximum number of bits that can be present in respective fingerprints of candidate structures in order for a candidate structure to be considered a match for the query structure, and traversing the inverted index to identify candidate structures having fingerprints with a number of bits in between the minimum number of bits and the maximum number of bits, including rejecting as candidates any chemical structures that have fingerprints having fewer than the minimum number of bits or having greater than the maximum number of bits.

In some implementations, the inverted index further includes a plurality of bit count posting lists, each bit count posting list corresponding to a number of bits that are set in each fingerprint map, and wherein each bit count posting list is associated with all structures in the collection of chemical structures having a fingerprint map with a number of bits that are set corresponding to the respective bit count of the bit count posting list.

In some implementations, traversing the inverted index to identify candidate structures includes sorting a plurality of posting list identifiers according to a current structure identifier of each bit term posting list to generate a sorted list of posting list identifiers, traversing the bit count posting lists to identify a current candidate structure identifier, wherein the current candidate structure identifier is associated with a current candidate structure having a fingerprint with greater than the minimum number of bits and less than the maximum number of bits, designating a particular posting list identifier at a position in the sorted list corresponding to the minimum number of bits as a pivot term posting list, designating the current structure identifier of the pivot term posting list as a current pivot structure identifier, and selecting a next bit term posting list to advance based on the current pivot structure identifier.

In some implementations, selecting a next bit term posting list to advance includes determining that the current pivot structure identifier is less than the current candidate structure identifier and that the current pivot structure identifier is not equal to the current candidate structure identifier, and in response, advancing the pivot term posting list so that the current structure identifier is equal to or greater than the current candidate structure identifier.

In some implementations, selecting a next bit term posting list includes determining that the current pivot structure identifier is greater than the current candidate structure identifier and that the current pivot structure identifier is not equal to the current candidate structure identifier, and in response, advancing each bit count posting list to a structure identifier that is equal to the current pivot structure identifier, and updating the current candidate structure identifier to the current pivot structure identifier.

In some implementations, the method further includes computing a minimum number of matching bits for the current candidate structure based on a number of bits that are set in the fingerprint map of the candidate structure.

In some implementations, the method further includes computing a number of matching bits for the current candidate structure.

In some implementations, the method further includes selecting a bit term posting list to advance based on the current candidate structure identifier.

In some implementations, computing a number of matching bits for the current candidate structure includes determining that the current candidate structure identifier is equal to the current structure identifier of the bit term posting list, and in response, increasing the number of matching bits for the current candidate structure.

In some implementations, computing a number of matching bits for the current candidate structure includes determining that the current candidate structure identifier is not equal to the current structure identifier of the bit term posting list, and in response, determining a number of remaining bit term posting lists with respective current structure identifiers less than the current candidate structure identifier.

In some implementations, the method further includes determining that the number of remaining bit term posting lists is sufficient to reach the minimum number of matching bits, and in response, selecting a bit term posting list to advance based on the current candidate structure identifier.

In some implementations, the method further includes determining that the number of remaining bit term posting lists is insufficient to reach the minimum number of matching bits, and in response, traversing the bit count posting lists to identify a new current candidate structure identifier.

In some implementations, the method further includes computing a score of the current candidate structure from the number of matching bits and the number of bits set in the fingerprint map of the current candidate structure.

In some implementations, the method further includes identifying the current candidate structure as a candidate structure.

In some implementations, the method further includes traversing the bit count posting lists to identify a new current candidate structure identifier.

In some implementations, the method further includes while traversing the inverted index, determining an updated target score threshold for a current set of top-scoring candidate structures, and rejecting candidate structures having a score that does not satisfy the updated target score threshold.

According to a second aspect, there is provided a system including: one or more computers; and one or more storage devices communicatively coupled to the one or more computers, where the one or more storage devices store instructions that, when executed by the one or more computers, cause the one or more computers to perform the operations of the respective method of any preceding aspect.

According to a third aspect, there are provided one or more non-transitory computer storage media storing instructions that when executed by one or more computers cause the one or more computers to perform the operations of the respective method of any preceding aspect.

Particular embodiments of the subject matter described in this specification can be implemented so as to realize one or more of the following advantages.

The cheminformatics platform described in this specification can search the collection of structures more quickly and efficiently than conventional methods, while maintaining the ability to compose chemical structure queries with other querying capabilities. For example, when executing fingerprint-based similarity scoring for a query structure, conventional methods may use a disjunctive comparison to compare the query fingerprint with fingerprint maps of other chemical structures. However, some fingerprint bits are vastly more common than others and thus may match an extremely large number of chemical structures. As a result, a conventional disjunctive comparison may end up scoring a majority of chemical structures in the database, nearly all of which have no chance of meeting a target similarity threshold.

In contrast, the cheminformatics platform described in this specification can compute a minimum number of bits and a maximum number of bits that can be present in fingerprints of candidate structures in the collection of chemical structures. The cheminformatics platform can traverse posting lists efficiently to identify candidate structures by rejecting as candidates any chemical structures that have fingerprints with fewer than the minimum number of bits or with greater than the maximum number of bits to reduce the number of chemical structures that are searched and scored. This allows the cheminformatics platform described in this specification to perform similarity searches nearly instantaneously on entire structure databases of unbounded size. For sub-structure search, the cheminformatics platform can also more efficiently perform the fingerprint screening phase by dropping bits that do not provide high filtering power, for example. Thus the techniques described in this specification can reduce the number of comparisons in the fingerprint screening phase, leading to more efficient computational performance. In addition, the cheminformatics platform can perform a sub-structure search process only on the candidate structures. The cheminformatics platform can thus reduce the computing time and computing resources needed to respond to the user's request.

The cheminformatics platform described in this specification can perform highly sophisticated similarity searches nearly instantaneously on entire structure databases of unbounded size. For example, the cheminformatics platform can generate an index having posting lists that each correspond to a bit in the fingerprint maps of chemical structures in the structure databases. The index format and search algorithms used by the cheminformatics platform are naturally horizontally scalable. For example, the cheminformatics platform can store the index across multiple nodes and multiple shards, and process each shard independently. The cheminformatics platform can include larger numbers of nodes and shards to store an index for larger databases of structures.

The cheminformatics platform described in this specification can provide for different types of queries. A user of the cheminformatics platform may want to find structures in the collection of chemical structures that have similar properties of different types to a known query structure, for example. The cheminformatics platform can also search for and provide structures in a collection of structures that include sub-structures of a query structure. The cheminformatics platform can also provide a measure that indicates how similar a candidate structure is to the query structure.

The cheminformatics platform described in this specification provides for flexibility in responding to a request. For example, the cheminformatics platform can receive a request that specifies a query structure, and obtain a query fingerprint for the query structure. The cheminformatics platform can support different types of query fingerprints. In some implementations, the cheminformatics platform can receive or generate different types of fingerprint maps, obtain query fingerprints of different types for a query structure, and traverse the posting lists using the different types of query fingerprints. The cheminformatics platform can thus support different types of features or constraints, such as including or excluding stereochemistry information in the fingerprint. In addition, the cheminformatics platform can use different scoring metrics for similarity scores, such as Tanimoto, Dice, etc., for which the cheminformatics platform can compute bit bounds based on the target score threshold and query fingerprint.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
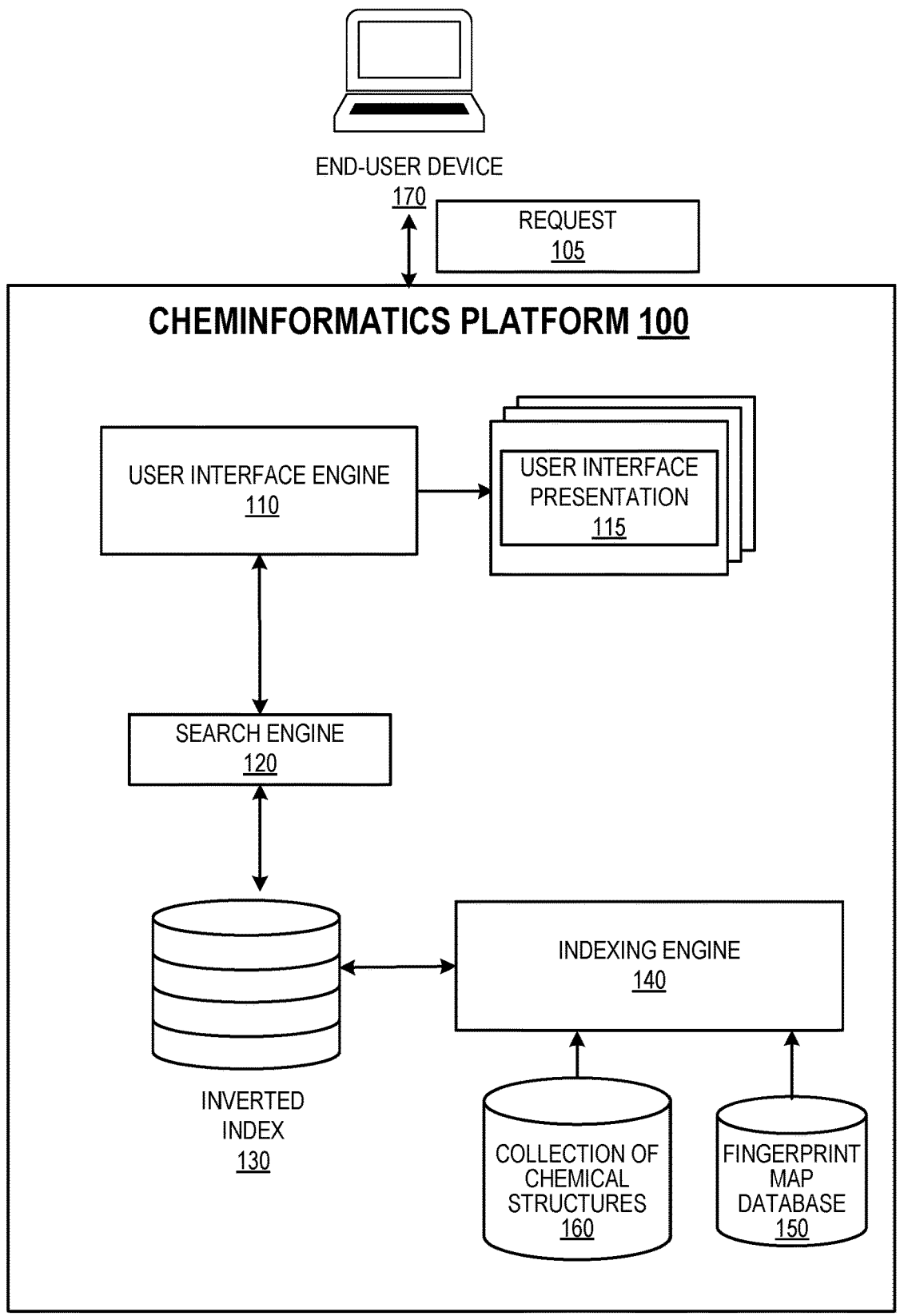
FIG. 1 is a block diagram of an example cheminformatics platform that can query a collection of structures.

FIG. 1 is a block diagram of an example cheminformatics platform 100 that can query a collection of structures. The cheminformatics platform 100 is an example of a system implemented as computer programs on one or more computers in one or more locations in which the systems, components, and techniques described below are implemented.

The cheminformatics platform 100 can receive a request 105 that specifies a query structure and identify a chemical structure in the collection of chemical structures 180 that matches the query structure. A matching chemical structure can be a chemical structure that is similar to the query structure, or that includes sub-structures of the query structure, for example. A chemical structure that is similar to the query structure can be a chemical structure that has a similarity score that satisfies a threshold similarity score, for example. A chemical structure that is similar to the query structure that has a similarity score that is within the top-N chemical structures with the highest similarity scores, where N is an integer greater than one, for example. For example, if the query structure is a compound, the cheminformatics platform 100 can provide a tautomer of the compound that exists in the collection of chemical structures 160. For example, the tautomer can have the same molecular formula as the compound, but with different connectivity. The cheminformatics platform 100 can also search for structures that are sub-structures of a query structure. The cheminformatics platform 100 can also provide a measure that indicates how similar a candidate structure is to the query structure.

The cheminformatics platform 100 can be a distributed cloud-based computing system that includes: (i) a user interface engine 110, (ii) a user interface presentation 115, (iii) a search engine 120, (iv) an inverted index 130, (v) an indexing engine 140, (vi) a fingerprint map database 150, and (vii) a collection of chemical structures 160.

The cheminformatics platform 100 can be configured to receive the request 105. The cheminformatics platform 100 can receive the request 105 from, e.g., a user of an end-user device 170, or in any other appropriate manner. As a particular example, the user of the end-user device 170 can provide the request 105 by way of an input into a user interface (e.g., a graphical user interface, GUI), or an application programming interface (API), made available by the cheminformatics platform 100 or the end-user device 170.

The cheminformatics platform 100 includes the user interface engine 110. The user interface engine 110 is configured to generate a user interface presentation 115 that displays the results of the search performed by the search engine 120. The user interface engine 110 can generate the user interface presentation 110 that presents, to a user of the end-user device 170 for example, data representing a chemical structure in the collection of chemical structures that matches the query structure. For example, the user interface presentation 115 can include a visualization of the identified chemical structure.

The cheminformatics platform 100 can provide the user interface presentation 115 for display to a user of the end-user device 170. Generally, the end-user device 170 can be an electronic device that is capable of requesting and receiving content over the network described above, e.g., the Internet. The end-user device 170 can include any client computing device such as a laptop/notebook computer, wireless data port, smart phone, personal data assistant (PDA), tablet computing device, one or more processors within these devices, or any other suitable processing device that can send and receive data over the network. For example, the end-user device 170 can include, e.g., a computer that includes an input device, such as a keypad, touch screen, or other device that can accept user information, and an output device that conveys information, including digital data, visual information, and/or the user interface presentation 115.

The end-user device 170 can include one or more client applications. A client application is any type of application that allows the end-user device 170 to request and view content on a respective client device. Generally, a user of the end-user device 170, such as a researcher in a laboratory, can use the client application to query a collection of chemical structures for similar structures to a query structure. For example, the researcher may want to analyze chemical structures with similar structural properties as the query structure. The researcher can use the client application to input data representing the query structure. The cheminformatics platform 100 can provide data representing the query structure to the search engine 120, and the search engine 120 can provide data representing similar chemical structures in the collection of chemical structures to the client application. The client application can provide the data representing similar chemical structures to the user, for example, by displaying a visualization of each similar chemical structure.

In some implementations, a client application can use parameters, metadata, and other information received, e.g., at launch, to access a particular set of data from the cheminformatics platform 100. For example, a researcher in a particular laboratory can use the client application to limit the search to chemical structures that are available in the laboratory.

The collection of chemical structures 160 can include data that specifies any appropriate number of chemical structures. For example, the collection of chemical structures 160 can include tens, hundreds, thousands, millions, or billions of chemical structures. The collection of chemical structures 160 can include data representing the chemical structure of each chemical structure, for example. The cheminformatics platform 100 can obtain the data representing chemical structures from a database, or in any other appropriate manner.

The fingerprint map database 150 can include fingerprint maps for the chemical structures in the collection of chemical structures 160. For example, the fingerprint map database 150 can include a fingerprint map for each chemical structure of the collection of chemical structures 160. Each fingerprint map can include multiple bit terms. For example, the fingerprint map can be a vector with multiple bit terms. Each bit term or combination of bit terms can represent a different feature of multiple features of the associated chemical structure. For example, a particular type of fingerprint map may be associated with a particular set of features. Each fingerprint map in the fingerprint map database 150 can thus include bit terms that represent that particular set of features. A different type of fingerprint map may be associated with different sets of features. In some implementations, the fingerprint map database 150 can include fingerprint maps of different types for each chemical structure. Examples of fingerprint maps of different types include those described in Jingbo Yang, Yiyang Cai, Kairui Zhao, Hongbo Xie, Xiujie Chen, Concepts and applications of chemical fingerprint for hit and lead screening, Drug Discovery Today, Volume 27, Issue 11, 2022, 103356, ISSN 1359-6446.

The cheminformatics platform 100 can use the indexing engine 140 to generate the inverted index 130. For example, the indexing engine 140 can access the collection of chemical structures 160. For each chemical structure in the collection of chemical structures 160, the indexing engine 140 can obtain an associated fingerprint map from the fingerprint map database 150. The indexing engine 140 can process the fingerprint maps to generate posting lists. For example, the indexing engine 140 can generate bit term posting lists. In some implementations, the indexing engine 140 can generate bit count posting lists.

The inverted index 130 can include multiple bit term posting lists. Each bit term posting list can correspond to one of the bit terms that are found in the fingerprint maps of the fingerprint map database 150. For example, the inverted index 130 can include a bit term posting list for each bit term that can be found in the fingerprint map database 150. Each bit term posting list can be associated with all chemical structures in the collection of chemical structures 160 that have a feature corresponding to the bit term of the bit term posting list. For example, a bit term posting list for a particular bit term can include a list of any chemical structures in the collection of chemical structures 160 that have the particular bit term in their associated fingerprint map. Example bit term posting lists are discussed below with reference to FIG. 3.

In some implementations, the inverted index 130 can also include multiple bit count posting lists. Each bit count posting list can correspond to a number of bits that are set in each of the fingerprint maps. For example, the inverted index 130 can include a bit count posting list for each different number of bits that are set in each fingerprint map. Each bit count posting list can be associated with all chemical structures in the collection of chemical structures 160 that have a fingerprint map with a number of bits that are set corresponding to the bit count of the bit count posting list. For example, a bit count posting list for a particular bit count can include a list of any chemical structures in the collection of chemical structures 160 that have the particular bit count of bits that are set in their associated fingerprint map.

The cheminformatics platform 100 can further include the search engine 120 that is configured to carry out one or more tasks associated with the request 105. For example, the search engine 120 can include one or more software application programs executable within the cheminformatics platform 100 that can search the collection of chemical structures 160 for candidate structures that are similar to the query structure in the request 105. For example, the search engine 120 can search the collection of chemical structures 160 for candidate structures by traversing the inverted index 130.

Thus, in order to provide data representing a matching structure to a user, upon receiving the request 105 that specifies a query structure from the end-user device 170, the cheminformatics engine 100 can obtain a query fingerprint for the query structure. The query fingerprint can include a bit vector that includes bit terms that represent features that are present in the query structure. The query fingerprint can include bit terms that represent the same set of features as the fingerprint maps of the fingerprint map database 150. That is, the query fingerprint can be the same type of fingerprint map as the fingerprint maps of the fingerprint map database 150. The cheminformatics engine 110 can use the search engine 120 to compute, based on the query fingerprint and a target score threshold, a minimum number of bits that must be present in the fingerprints of candidate structures in the collection of chemical structures 160 in order for a candidate structure to be considered a match for the query structure. The search engine 120 can also compute, based on the query fingerprint and the target score threshold, a maximum number of bits that can be present in fingerprints of the candidate structures in order for a candidate structure to be considered a match for the query structure.

The search engine 120 can then traverse the inverted index 130 to identify candidate structures having fingerprints with a number of bits between the minimum number of bits and maximum number of bits matching the query fingerprint. For example, the search engine 120 can reject as candidates any chemical structures that have fingerprints having fewer than the minimum number of bits or having greater than the maximum number of bits. The cheminformatics platform 100 can provide data representing the candidate structures to the user through the user interface engine 110.

Figure 2:
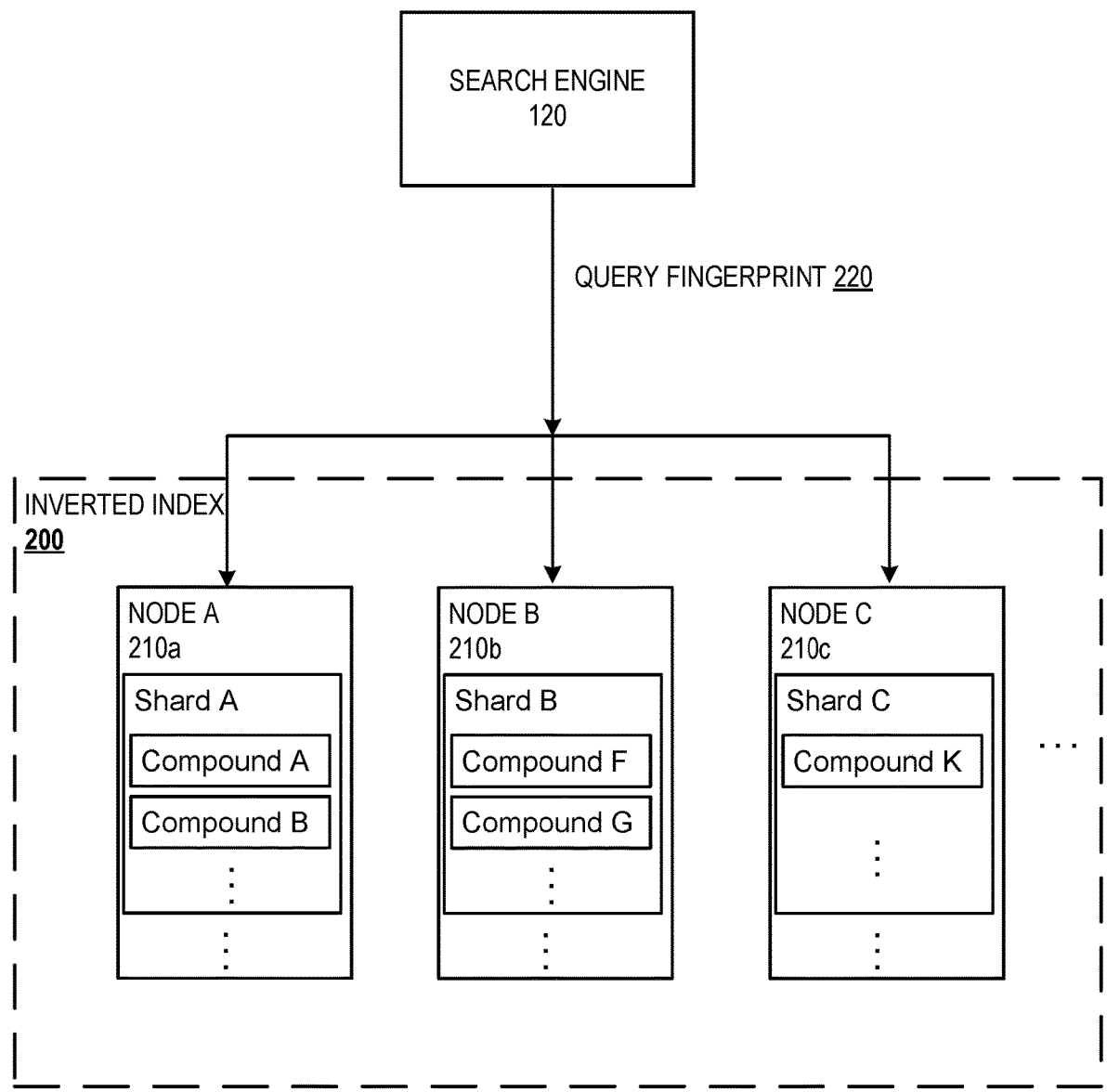
FIG. 2 illustrates an example inverted index stored across nodes.

FIG. 2 illustrates an example inverted index 200 stored across nodes. The inverted index 200 is an example of the inverted index 130 described above with reference to FIG. 1. In the example of FIG. 2, the inverted index 200 is split over multiple nodes 210. For example, each node 210a, 210b, and 210c can include multiple shards. In some implementations, each node can be stored on a separate server.

Each shard can include data representing one or more chemical structures. For example, shard A stores data representing at least structure A and structure B. Shard B stores data representing at least structure F and structure G. Shard C stores data representing at least structure K. In some examples, each node 210 can include more than one shard. Thus, the collection of chemical structures 160 and the inverted index 130 of FIG. 1 can be split among different nodes 210, allowing for horizontal scalability. For example, splitting among different nodes can allow for efficient searching, parallelization, and redundancy.

Each node can also have one or more posting lists for structures belonging to the shard assigned to the node. In the example of FIG. 2, each node can store bit term posting lists. For example, shard A can include bit term posting lists for bit terms that are associated with the fingerprint of structure A and the fingerprint of structure B. For example, if structure A has bit term 1 set, shard A can include the bit term 1 posting list. In some implementations, the shard can include bit term posting lists for all bit terms that are associated with the fingerprint maps of all chemical structures. For example, the shard can include bit term posting lists for all bit terms that can be found in the fingerprint map database 150 of FIG. 1.

As described above with reference to FIG. 1, a system such as the cheminformatics platform 100 can receive a request to search the inverted index 200 for matching chemical structures. The request can specify a query structure representing a chemical structure that includes one or more molecules. The cheminformatics platform 100 can obtain a query fingerprint 220 for the query structure. For example, the cheminformatics platform 100 can use the same type of fingerprint map that the posting lists of the inverted index 200 were generated from. The search engine 120 can search the inverted index 200 using the query fingerprint 220.

The search engine 120 can compute a minimum number of bits that must be present in fingerprints of candidate structures in the collection of chemical structures 160 in order for a candidate structure to be considered a match for the query structure based on the query fingerprint 220 and a target score threshold. The target score threshold can be used to define the number of matching bit terms required for a candidate structure to be considered a match. The search engine 120 can also compute a maximum number of bits that must be present in fingerprints of candidate structures in order for a candidate structure to be considered a match for the query structure based on the query fingerprint 220 and the target score threshold. For example, the target score threshold can be a target similarity score. For example, the target score threshold can be a Tanimoto score. The Tanimoto score represents a measure of similarity between a chemical structure and the query structure associated with the query fingerprint 220. For example, the Tanimoto score between a query structure and a potential candidate structure can be calculated as: $|Q \cap T|/|Q \cup T|$ where Q represents the query fingerprint 220 and T represents the fingerprint map for the potential candidate structure. That is, the Tanimoto score can be the ratio of the number of common bits set to "1" to the total number of bits set to "1" in the fingerprint map for the query structure and the fingerprint map for the potential candidate structure.

Given a threshold Tanimoto score, the search engine 120 can compute bounds on the number of bits that must be set or present in fingerprints of candidate structures in order for the candidate structures to each have Tanimoto scores greater than or equal to the threshold Tanimoto score. Thus, any chemical structure in the collection of chemical structures that includes a number of bits that is less than the minimum number of bits, or a number of bits that is greater than the maximum number of bits, can be rejected as a candidate structure because they have Tanimoto scores that are less than the threshold Tanimoto score. In some implementations, the system can use other types of scoring such as Tversky scores.

Figure 3:
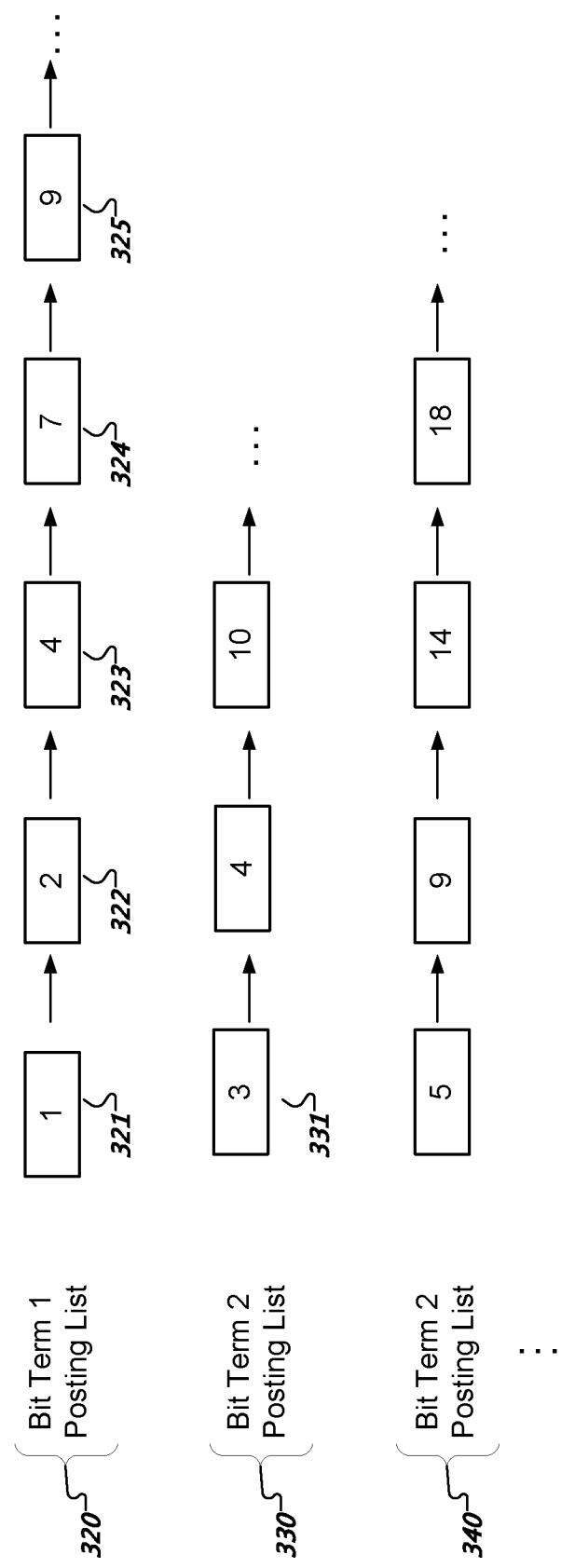
FIG. 3 illustrates example bit term posting lists of an example inverted index.

FIG. 3 illustrates example bit term posting lists 320, 330, and 340. The example bit term posting lists 320, 330, and 340 correspond to individual bit terms. Each bit term posting list in FIG. 3 includes a list of chemical structures that include the corresponding bit term in their fingerprint maps. For example, the list of chemical structures can be a subset of the chemical structures in the collection of chemical structures 160 of FIG. 1.

Each bit term posting list 320, 330, and 340 corresponds to a bit term. For example, the bit terms correspond to individual bits of a fingerprint map of the same type as a query fingerprint. For example, bit term posting list 320 includes a list of structures that have a "1" for bit term 1, or at the first bit position, in their query fingerprints. Bit term posting list 330 includes a list of structures that have a "1" for bit term 2, or at the second bit position, in their query fingerprints. Bit term posting list 340 includes a list of structures that have a "1" for bit term 3, or at the third bit position, in their query fingerprints.

The list of structures can be identified by a structure identifier, for example. For example, bit term posting list 320 includes structure identifiers 321, 322, 323, 324, and 325. Structure identifier 321 indicates that the structure with the structure identifier 1 includes a "1" at bit term 1 in its fingerprint map, for example. Similarly, structure identifiers 322, 323, 324, and 325 indicate that the corresponding structures 2, 4, 7, and 9 include a "1" at bit term 1 in their fingerprint maps.

A search engine such as the search engine 120 of FIG. 1 can traverse the bit term posting lists 320, 330, and 340 of the inverted index to identify candidate structures having fingerprints with a number of bits in between the minimum number of bits and the maximum number of bits. For example, the search engine can reject, as candidates, any chemical structures that have fingerprints with fewer than the minimum number of bits or with greater than the maximum number of bits.

The search engine 120 can maintain the bit term posting lists 320, 330, and 340 in a sorted order by structure identifiers. For example, FIG. 3 shows that each bit term posting list 320, 330, and 340 includes a list of structures in increasing order by structure identifiers. In some implementations, each posting list can be stored across different blocks. Each posting list can include information about the chemical structures in each block in the posting list. For example, a posting list can include statistics such as the maximum norm for all chemical structures in a particular block. In these implementations, the search engine 120 can skip over entire blocks of a posting list without accessing the individual chemical structures stored in the posting list.

As another example, each block can include statistics such as the norms for the minimum and maximum number of bits for fingerprint maps for chemical structures in the block. In these implementations, the search engine 120 can skip over entire blocks where all structures in the block are outside of the range between the minimum number of bits and maximum number of bits.

The search engine 120 can traverse the inverted index as described in further detail below with reference to FIGS. 5A-5C. For example, the search engine 120 can sort posting list identifiers, designate a particular posting list identifier as a pivot term posting list, designate a current pivot structure identifier, and select a next posting list to advance based on the current pivot structure identifier.

Figure 4:
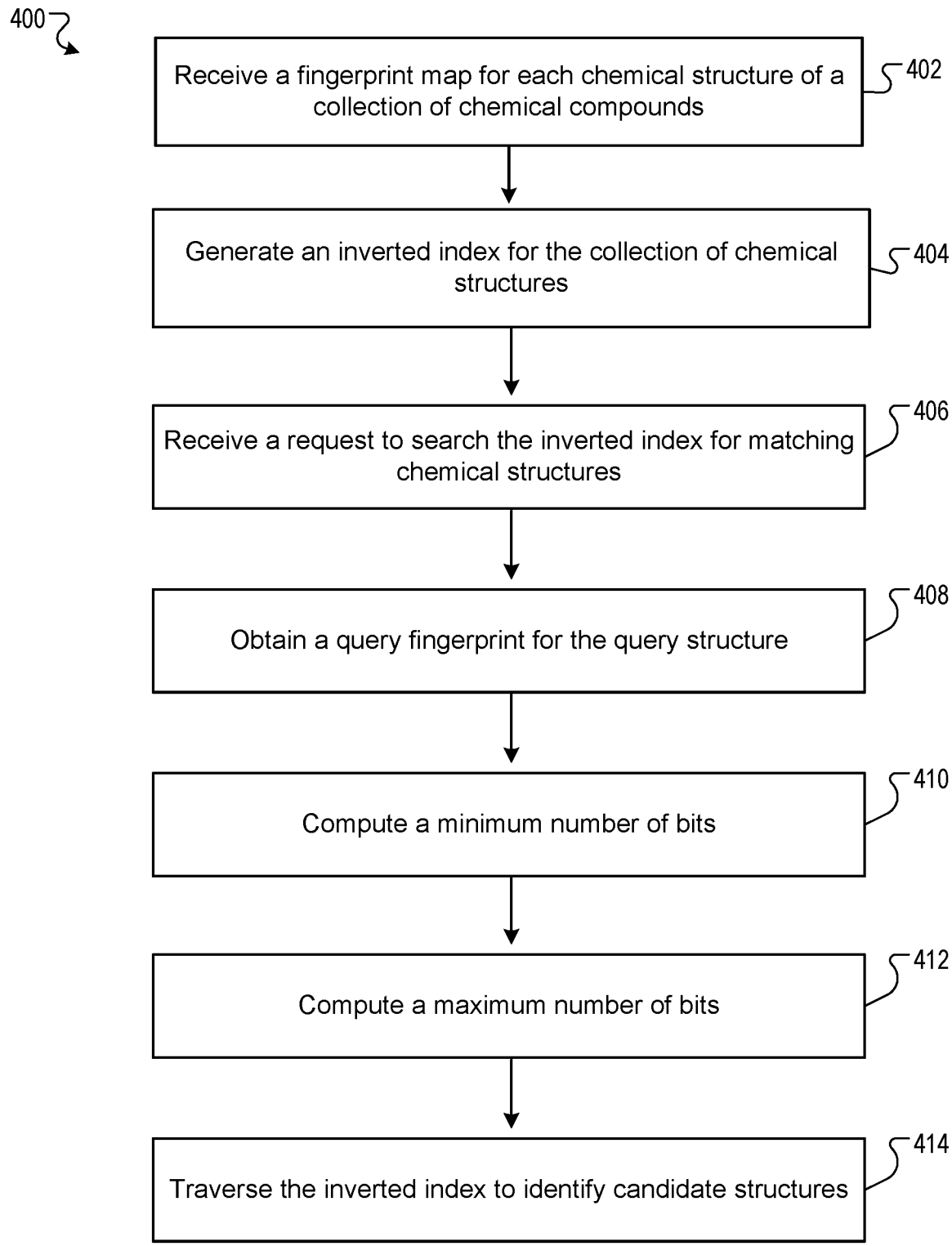
FIG. 4 is a flow diagram of an example process for identifying candidate structures for a query structure for a similarity search.

FIG. 4 is a flow diagram of an example process 400 for identifying candidate structures for a query structure. For convenience, the process 400 is described as being performed by a system of one or more computers located in one or more locations. For example, a cheminformatics platform, e.g., the cheminformatics platform 100 of FIG. 1, appropriately programmed in accordance with this specification, can perform the process 400.

The system receives a fingerprint map for each chemical structure of a collection of chemical structures (402). The fingerprint map includes multiple bit terms, and each bit term represents a different feature of multiple features of the chemical structure. In some implementations, the system can receive multiple fingerprint maps, each of a different type, for each chemical structure of a collection of chemical structures. For example, a fingerprint map of a particular type can represent a particular set of features.

The system generates an inverted index for the collection of chemical structures (404). The inverted index includes multiple bit term posting lists, and each bit term posting list corresponds to one of the bit terms. Each bit term posting list is associated with all structures in the collection of chemical structures having a feature corresponding to the respective bit term of the bit term posting list. For example, the inverted index can include a bit term posting list for each bit term that can be found among all the fingerprint maps for the collection of chemical structures.

In some implementations, the inverted index further includes multiple bit count posting lists. Each bit count posting list corresponds to a number of bits that are set in each fingerprint map. Each bit count posting list is associated with all structures in the collection of chemical structures that have a fingerprint map with a number of bits that are set corresponding to the respective bit count of the bit count posting list. For example, the inverted index can include a bit count posting list for each number of bits that are set for all the fingerprint maps for the collection of chemical structures.

The system receives a request to search the inverted index for matching chemical structures (406). The request can specify a query structure representing a chemical structure that includes one or more molecules. A matching chemical structure can be, for example, a chemical structure with similar properties, or a chemical structure that includes sub-structures of the query structure.

The system obtains a query fingerprint for the query structure (408). The query fingerprint can include a bit vector including bit terms representing which of the multiple features are present in the query structure. For example, the query fingerprint can be a fingerprint map of the same type as the fingerprint maps for the collection of chemical structures. That is, the query fingerprint can represent the same set of features as the fingerprint maps for the collection of chemical structures. In some implementations, the system can generate the query fingerprint for the query structure.

The system computes a minimum number of bits (410). The minimum number of bits can be the minimum number of bits that must be present in fingerprints of candidate structures in the collection of chemical structures in order for a candidate structure to be considered a match for the query structure. The system can compute the minimum number of bits based on the query fingerprint and the target score threshold. For example, the target score threshold can be used to compute a number of matching bits between the query structure and a candidate structure in order for the candidate structure to be considered a match for the query structure.

The system computes a maximum number of bits (412). The maximum number of bits can be the maximum number of bits that can be present in fingerprints of the candidate structures in order for a candidate structure to be considered a match for the query structure. The system can compute the maximum number of bits based on the query fingerprint and the target score threshold.

The system can compute the minimum number of bits that must be present in fingerprints of candidate structures based on the target score threshold. The system can also compute the maximum number of bits that can be present in fingerprints of candidate structures based on the target score threshold. For example, the system can receive a default target score threshold. In some implementations, the system can generate the target score threshold. The target score threshold can represent a similarity score, for example. As an example, the target score threshold can be a Tanimoto score. The system can use Tanimoto scoring to determine a minimum number of bits and a maximum number of bits based on the Tanimoto score. In some implementations, the target score threshold can be another similarity score such as a Tversky score or a Dice score, to name just a few examples.

As an example, the system can compute the minimum number of bits by assuming that every bit in a fingerprint map of a candidate structure matches a bit in the query fingerprint. The system can determine what the shortest candidate fingerprint length must be in order to reach the target score threshold. For example, the system can use a target score threshold calculated as the number of matching bits between a query fingerprint and a candidate fingerprint, divided by the sum of the darkness of the query fingerprint and the darkness of the candidate fingerprint, subtracted by the number of matching bits. Thus the system can assume the number of matching bits is the darkness of the candidate fingerprint, and use the target score threshold and darkness of the candidate fingerprint to compute the darkness of the candidate fingerprint. In these implementations, the darkness of the candidate fingerprint is equivalent to the minimum number of bits. The darkness of a fingerprint can refer to the number of bits that are set to "1" in the fingerprint map.

The system traverses the inverted index to identify candidate structures (414). The system can traverse the bit term posting lists of the inverted index to identify candidate structures having fingerprints with a number of bits in between the minimum number of bits and the maximum number of bits. For example, the system can reject as candidates any chemical structures that have fingerprints having fewer than the minimum number of bits or having greater than the maximum number of bits. In some implementations, the system can traverse the inverted index as described with reference to FIGS. 5A-5C.

In some implementations, the system can perform a sub-structure search process to identify candidate structures that include a sub-structure of the query structure. For example, as described below with reference to FIG. 6, the sub-structure search process can include an atom-by-atom comparison between each identified candidate structure and the query structure.

Figure 5A:
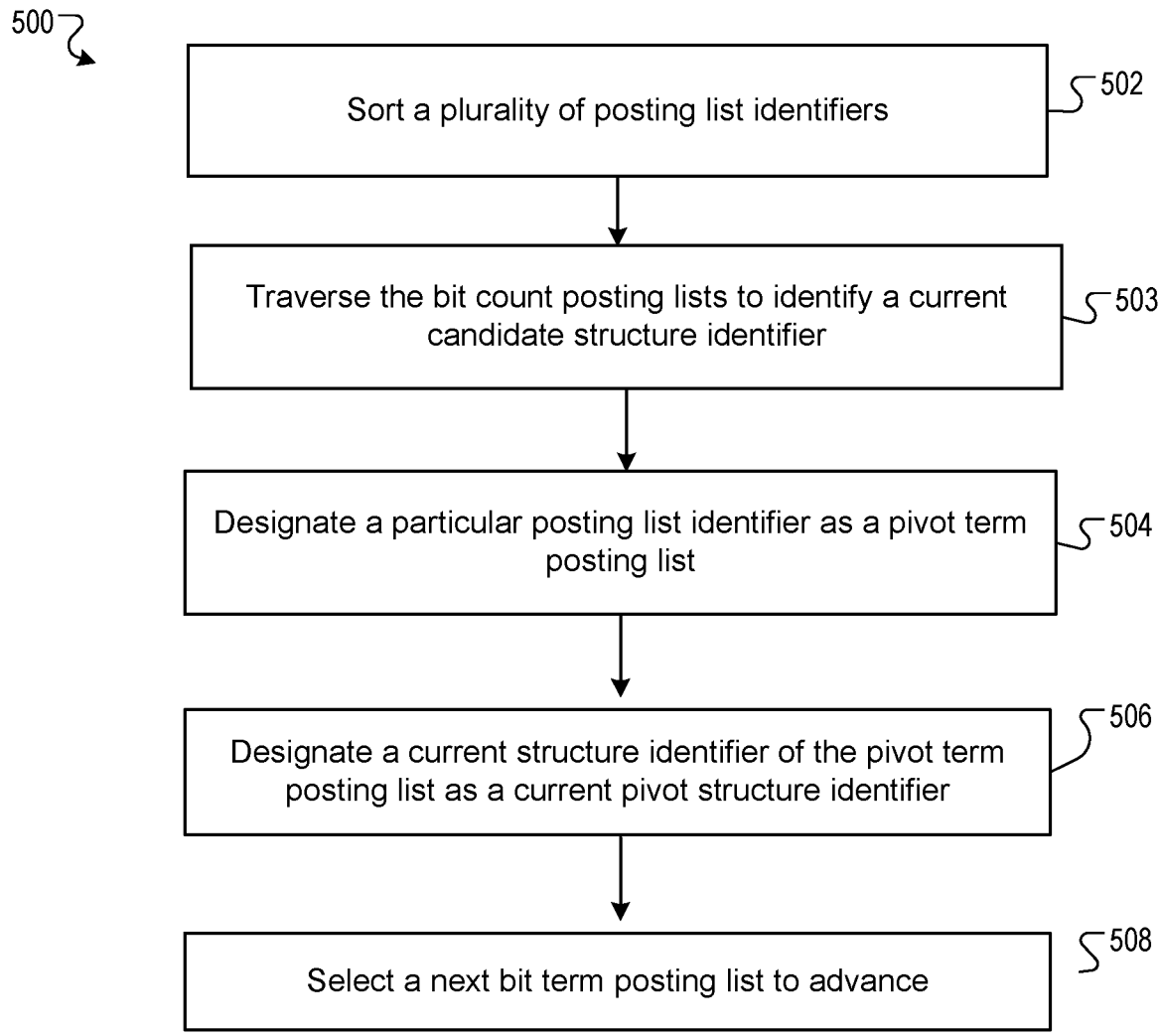
FIGS. 5A-5C depict a flow diagram of an example process for traversing the inverted index to identify candidate structures.
Figure 5B:
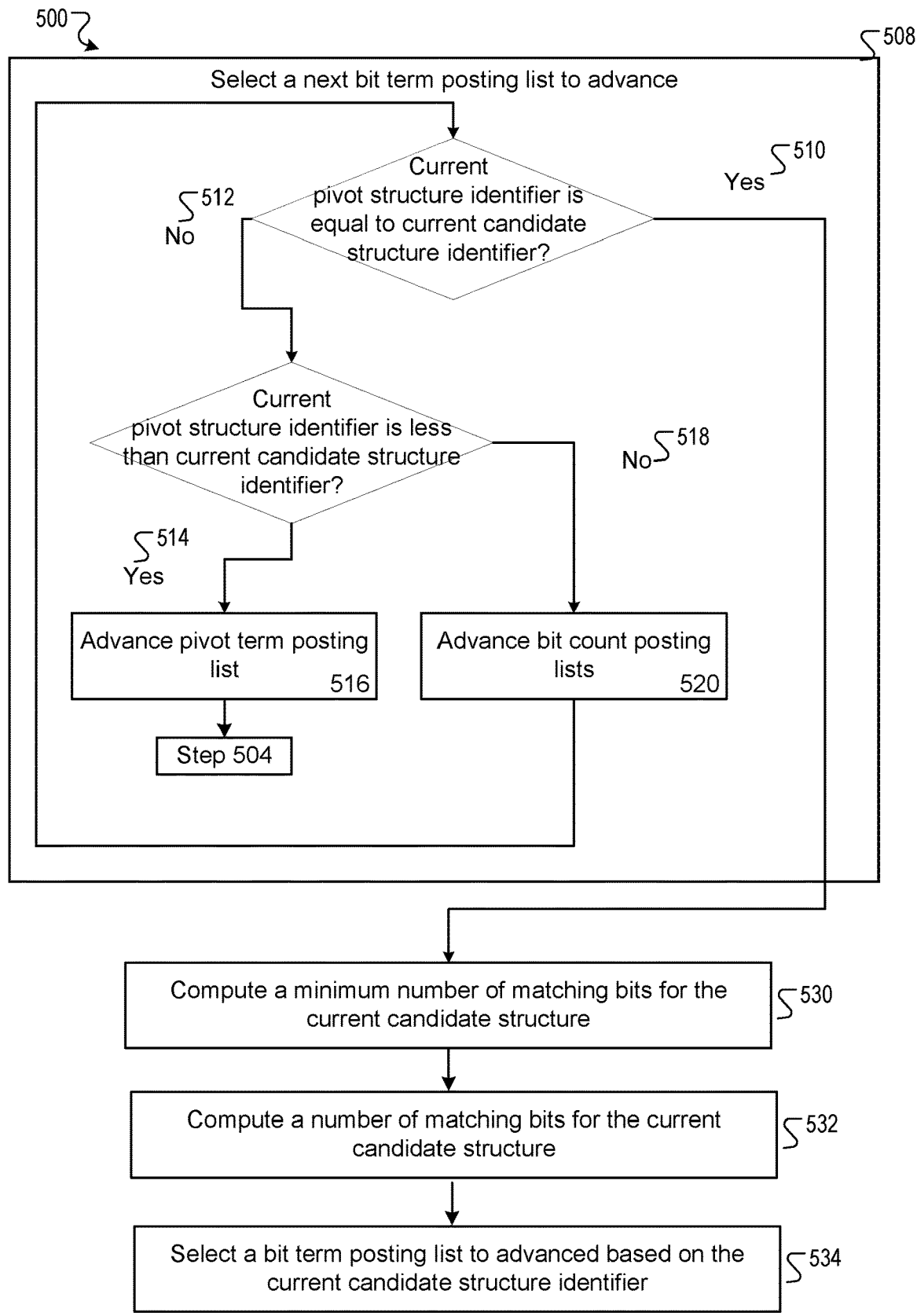
Figure 5C:
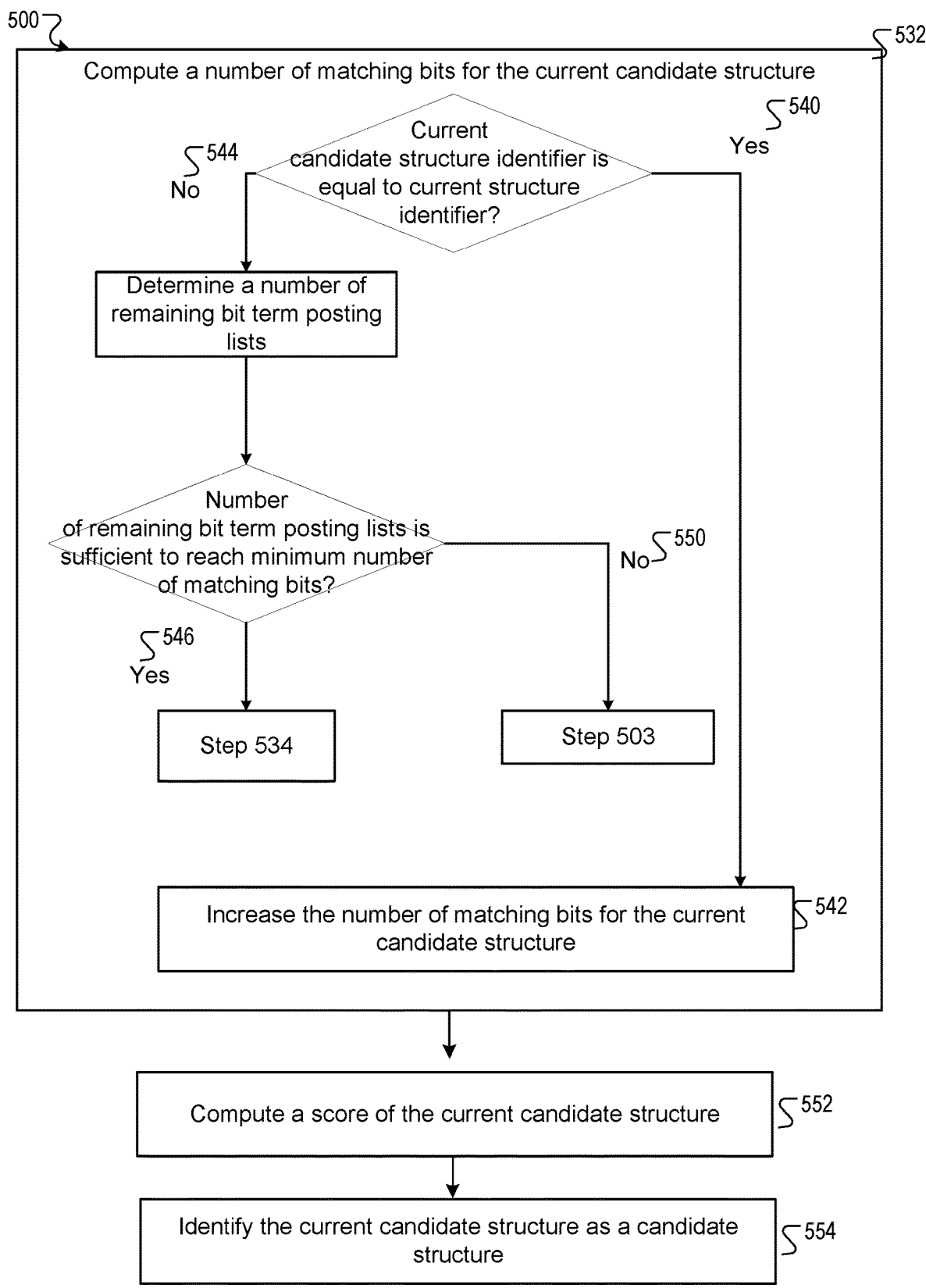

FIGS. 5A-5C depict a flow diagram of an example process 500 for traversing an inverted index. The system described above can perform the process 500 as part of step 414 of FIG. 4.

The system can sort a plurality of posting list identifiers (502). The system can sort the bit term posting lists according to a current structure identifier of each bit term posting list to generate a sorted list of posting list identifiers. For example, the current structure identifier of each bit term posting list can be the structure identifier of one of the chemical structures associated with the bit term posting list. As an example, referring to FIG. 3, the search engine 120 can sort the bit term posting lists for bit terms that are set in the query fingerprint 304. For example, for the bit vector 306, the search engine 120 can sort a bit term 3 posting list, a bit term 5 posting list, and a bit term 7 posting list. In some implementations, the search engine 120 can maintain information representing the sorted list of posting list identifiers, in a data structure, for example. In some implementations, the system can maintain the bit term posting lists in a priority queue.

The system can traverse the bit count posting lists to identify a current candidate structure identifier (503). The current candidate structure identifier can be associated with a current candidate structure that has a fingerprint with greater than the minimum number of bits and less than the maximum number of bits.

The system can designate a particular posting list identifier as a pivot term posting list (504). The system can designate a particular posting list identifier at a position in the sorted list corresponding to the minimum number of bits as a pivot term posting list.

The system can designate a current structure identifier of the pivot term posting list as a current pivot structure identifier (506). For example, the current pivot structure identifier can be one of the structure identifiers that is associated with the pivot term posting list. The system can select a next bit term posting list to advance (508). For example, the system can select a next bit term posting list to advance based on the current pivot structure identifier.

To select a next bit term posting list to advance, the system can compare the current pivot structure identifier to the current candidate structure identifier. For example, the system can determine that the current pivot structure identifier is equal to the current candidate structure identifier (510). In response, the system can perform process 500 starting at step 530.

The system can determine that the current pivot structure identifier is not equal to the current candidate structure identifier (512), and the current pivot structure identifier is less than the current candidate structure identifier (514). In response, the system can advance the pivot term posting list (516). For example, the system can advance the pivot term posting list so that the current structure identifier is equal to or greater than the current candidate structure identifier. That is, the current structure identifier for the pivot term posting list is now equal to the current candidate structure identifier. The system can then re-sort the bit term posting lists. The system can then perform process 500 starting at step 504.

The system can determine that the current pivot structure identifier is not equal to the current candidate structure identifier (512), and the current pivot structure identifier is greater than the current candidate structure identifier (518). In response, the system can advance the bit count posting lists (520). For example, the system can advance each bit count posting lists to a structure identifier that is equal to the current pivot structure identifier. The system can then update the current candidate structure identifier to the current pivot structure identifier, and perform process 500 starting at step 508.

The system can compute a minimum number of matching bits for the current candidate structure (530). For example, the system can compute the minimum number of matching bits for the current candidate structure based on a number of bits that are set in the fingerprint map of the candidate structure. In some implementations, the system can compute the minimum number of matching bits based on a score, such as the Tanimoto score.

As an example, the system can compute the minimum number of matching bits using a target score threshold calculated as the number of matching bits between a query fingerprint and a candidate fingerprint, divided by the sum of the darkness of the query fingerprint and the darkness of the candidate fingerprint, subtracted by the number of matching bits. Thus the system can use the target score threshold, darkness of the candidate fingerprint, and darkness of the query fingerprint to compute the minimum number of matching bits.

The system can compute a number of matching bits for the current candidate structure (532). For example, the system can initialize the number of matching bits for the current candidate structure to one, for the bit term associated with the pivot term posting list.

The system can select a bit term posting list to advance based on the current candidate structure identifier (534). For example, the system can choose a bit term posting list for which the current structure identifier is lower than the current candidate structure identifier to advance. The system can advance the current structure identifier to the next structure identifier that is equal to or greater than the current candidate structure identifier.

To compute the number of matching bits for the current candidate structure, the system can compare the current candidate structure identifier and the current structure identifier of the bit term posting list selected in step 534. The system can determine that the current candidate structure identifier is equal to the current structure identifier of the bit term posting list (540). In response, the system can increase the number of matching bits for the current candidate structure (542). For example, the system can add one to the number of matching bits.

The system can determine that the current candidate structure is not equal to the current structure identifier of the bit term posting list (544). In response, the system can determine a number of remaining bit term posting lists (546). The remaining bit term posting lists can be bit term posting lists with respective current structure identifiers less than the current candidate structure identifier.

The system can determine that the number of remaining bit term posting lists is sufficient to reach the minimum number of matching bits (546). In response, the system can perform process 500 starting at step 534. That is, the system can select a bit term posting list to advance based on the current candidate structure identifier.

The system can determine that the number of remaining bit term posting lists is insufficient to reach the minimum number of matching bits (550). In response, the system can perform the process 500 starting at step 503. That is, the system can traverse the bit count posting lists to identify a new current candidate structure identifier.

The system can compute a score of the current candidate structure (552). The system can compute the score from the number of matching bits and the number of bits set in the fingerprint map of the current candidate structure.

The system can identify the current candidate structure as a candidate structure (554). For example, if the score of the current candidate structure is over a threshold similarity score, the system can identify the current candidate structure as a candidate structure.

The system can perform the process 500 starting at step 503. That is, the system can traverse the bit count posting lists to identify a new current candidate structure identifier.

In some implementations, while traversing the posting lists, the system can determine an updated target score threshold for a current set of top-scoring candidate structures. The system can reject candidate structures encountered while traversing the posting lists that have a score that does not satisfy the updated target score threshold. For example, the system can maintain data representing a similarity score for each candidate structure. The system may be configured to provide the top ten candidate structures with the highest similarity score to the query. After obtaining at least ten candidate structures, the system may sort the candidate structures by similarity score. The system can determine that the top ten candidate structures have similarity scores that are greater than the target score threshold. The system can thus determine an updated target score threshold that is higher than the target score threshold. The system can more efficiently traverse the posting lists by eliminating any searching done for chemical structures that will have similarity scores that are less than the similarity scores of the current group of top ten candidate structures.

Figure 6:
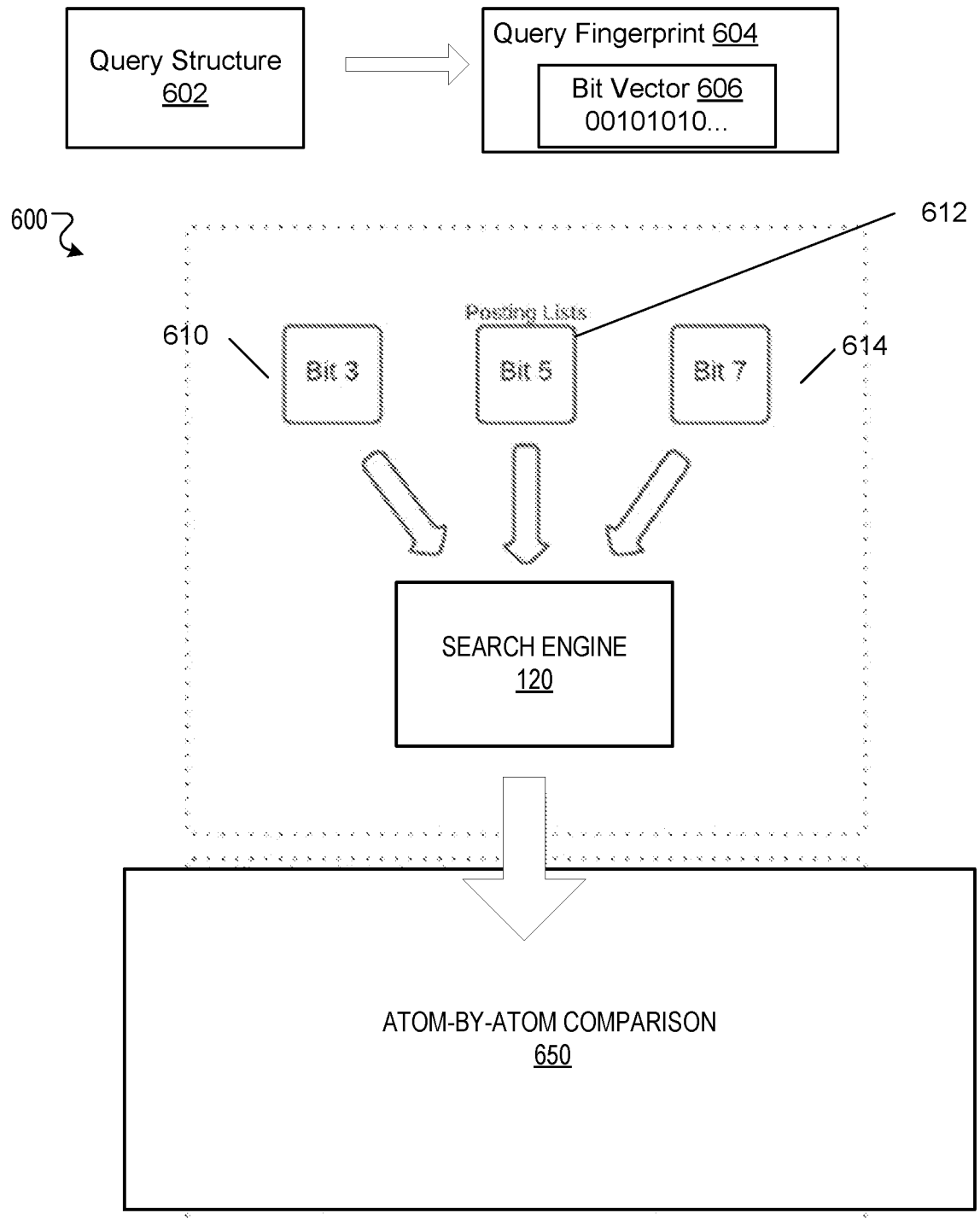
FIG. 6 is a diagram of an example process for querying a collection of chemical structures by sub-structure.

FIG. 6 is a diagram of an example process 600 for querying a collection of chemical structures by sub-structure. For convenience, the process 600 is described as being performed by a system of one or more computers located in one or more locations. For example, a cheminformatics platform, e.g., the cheminformatics platform 100 of FIG. 1, appropriately programmed in accordance with this specification, can perform the process 600. The process 600 can include a conjunction and an atom-by-atom search 650, for example.

The system can receive a query structure 602. For example, as described above, the query structure 602 can be specified in a request to search an inverted index for matching chemical structures.

The system can obtain a query fingerprint 604 for the query structure 602. An example query structure 602 can have an associated query fingerprint 604. For example, the query fingerprint 604 can be a fingerprint map for the query structure. The fingerprint map can be of the same type of fingerprint map as the fingerprint maps of the fingerprint map database 150 of FIG. 1. The query fingerprint 604 can include a bit vector 606. For example, each bit or combination of bits in the bit vector 606 can correspond to a feature of the query structure 602. In the example of FIG. 6, the bit vector starts with "00101010" and thus includes a "1" for bit term 3, bit term 5, and bit term 7.

As described above, the system can generate an inverted index for a collection of chemical structures. The inverted index can include multiple posting lists such as bit term posting lists 610, 612, and 614.

The system can perform a posting list conjunction. The search engine 120 can use the N shortest bit term posting lists of the bit term posting lists corresponding to the bit vector 606, where N is an integer greater than or equal to one, to identify candidate structures. For example, the search engine 120 can use the N shortest bit term posting lists out of the bit term posting lists 610, 612, and 614. The search engine 120 can use a conjunctive Boolean query to identify the candidate structures.

In some implementations, the system can exclude bits for comparison that do not provide high filtering power. For example, bit term 5 may have a long associated posting list. The system can thus not include the bit term 5 posting list 612 in the N shortest bit term posting lists.

In some examples, the request can specify a certain number of matching chemical structures. For example, the request may specify to search for the top-K matching structures ordered according to a particular sort key. In some implementations, the system can check the sort key of a structure that has passed fingerprint screening, i.e., been identified as a candidate structure. The system can determine whether the candidate structure falls within the current set of top-K matching structures based on the sort key. If the current candidate structure does not fall within the current set of top-K matching structures, the system can eliminate the identified candidate structure as a candidate structure. The system can thus skip the atom-by-atom comparison for the candidate structure.

The system can then perform the atom-by-atom comparison 650 on the identified candidate structures. In some implementations, the system can perform the atom-by-atom comparison 650 on the current set of top-scoring candidate structures. The identified candidate structures may have fingerprint maps that contain a subset or all of the same bits as the query fingerprint 604, but some of the identified candidate structures may be false positives. For example, a candidate structure and the query structure 602 may have similar features, but different sub-structures. The atom-by-atom comparison 650 can identify any candidate structures that match the query structure.

For example, the atom-by-atom comparison 650 can be a verification process that includes an atom-by-atom comparison between the chemical structure of the query structure 604 and each candidate structure. The system can obtain data representing the chemical structure of each candidate structure from the collection of chemical structures 160 of FIG. 1, for example.

The atom-by-atom comparison 650 can output a similarity score between the query structure 604 and each candidate structure, for example. In some implementations, the system can provide the top-scoring candidate structure with the highest similarity score for display at the end-user device 170 of FIG. 1. In some implementations, the system can provide more than one top-scoring candidate structure for display at the end-user device 170 of FIG. 1.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method comprising:
   receiving a fingerprint map for each chemical structure of a collection of chemical structures, wherein each fingerprint map comprises a plurality of bit terms, wherein each bit term of the plurality of bits represents a different respective feature of a plurality of features of the chemical structure;
   generating an inverted index for the collection of chemical structures, wherein the inverted index comprises a plurality of bit term posting lists, each bit term posting list corresponding to one of the bit terms, and wherein each bit term posting list is associated with all structures in the collection of chemical structures having a feature corresponding to the respective bit term of the bit term posting list, and wherein the inverted index further comprises a plurality of bit count posting lists, each bit count posting list corresponding to a number of bits that are set in each fingerprint map, and wherein each bit count posting list is associated with all structures in the collection of chemical structures having a fingerprint map with a number of bits that are set corresponding to the respective bit count of the bit count posting list;
   receiving a request to search the inverted index for matching chemical structures, wherein the request specifies a query structure representing a chemical structure comprising one or more molecules;
   obtaining a query fingerprint for the query structure, wherein the query fingerprint comprises a bit vector comprising bit terms representing which of the plurality of features are present in the query structure;
   computing, based on the query fingerprint and a target score threshold, a minimum number of bits that must be present in respective fingerprints of candidate structures in the collection of chemical structures in order for a candidate structure to be considered a match for the query structure;
   computing, based on the query fingerprint and the target score threshold, a maximum number of bits that can be present in respective fingerprints of candidate structures in order for a candidate structure to be considered a match for the query structure; and
   traversing the inverted index to identify candidate structures having fingerprints with a number of bits in between the minimum number of bits and the maximum number of bits, including rejecting as candidates any chemical structures that have fingerprints having fewer than the minimum number of bits or having greater than the maximum number of bits, comprising:
      sorting a plurality of posting list identifiers according to a current structure identifier of each bit term posting list to generate a sorted list of posting list identifiers;
      traversing the bit count posting lists to identify a current candidate structure identifier, wherein the current candidate structure identifier is associated with a current candidate structure having a fingerprint with greater than the minimum number of bits and less than the maximum number of bits;
      designating a particular posting list identifier at a position in the sorted list corresponding to the minimum number of bits as a pivot term posting list;
      designating the current structure identifier of the pivot term posting list as a current pivot structure identifier; and
      selecting a next bit term posting list to advance based on the current pivot structure identifier.

2. The method of claim 1, wherein selecting a next bit term posting list to advance comprises:
   determining that the current pivot structure identifier is less than the current candidate structure identifier and that the current pivot structure identifier is not equal to the current candidate structure identifier; and
   in response, advancing the pivot term posting list so that the current structure identifier is equal to or greater than the current candidate structure identifier.

3. The method of claim 1, wherein selecting a next bit term posting list to advance comprises:
   determining that the current pivot structure identifier is greater than the current candidate structure identifier and that the current pivot structure identifier is not equal to the current candidate structure identifier;

in response, advancing each bit count posting list to a structure identifier that is equal to the current pivot structure identifier; and updating the current candidate structure identifier to the current pivot structure identifier.

4. The method of claim 1, further comprising:

computing a minimum number of matching bits for the current candidate structure based on a number of bits that are set in the fingerprint map of the candidate structure.

5. The method of claim 4, further comprising:

computing a number of matching bits for the current candidate structure.

6. The method of claim 5, further comprising:

selecting a bit term posting list to advance based on the current candidate structure identifier.

7. The method of claim 6, wherein computing a number of matching bits for the current candidate structure comprises:

determining that the current candidate structure identifier is equal to the current structure identifier of the bit term posting list;

in response, increasing the number of matching bits for the current candidate structure.

8. The method of claim 6, wherein computing a number of matching bits for the current candidate structure comprises:

determining that the current candidate structure identifier is not equal to the current structure identifier of the bit term posting list;

in response, determining a number of remaining bit term posting lists with respective current structure identifiers less than the current candidate structure identifier.

9. The method of claim 8, further comprising:

determining that the number of remaining bit term posting lists is sufficient to reach the minimum number of matching bits; and in response, selecting a bit term posting list to advance based on the current candidate structure identifier.

10. The method of claim 8, further comprising:

determining that the number of remaining bit term posting lists is insufficient to reach the minimum number of matching bits; and in response, traversing the bit count posting lists to identify a new current candidate structure identifier.

11. The method of claim 5, further comprising:

computing a score of the current candidate structure from the number of matching bits and the number of bits set in the fingerprint map of the current candidate structure.

12. The method of claim 11, further comprising:

identifying the current candidate structure as a candidate structure.

13. The method of claim 12, further comprising:

traversing the bit count posting lists to identify a new current candidate structure identifier.

14. The method of claim 1, further comprising:

while traversing the inverted index, determining an updated target score threshold for a current set of top-scoring candidate structures; and rejecting candidate structures having a score that does not satisfy the updated target score threshold.

15. A system comprising:

one or more computers; and one or more storage devices storing instructions that are operable, when executed by the one or more computers, to cause the one or more computers to perform operations comprising:

receiving a fingerprint map for each chemical structure of a collection of chemical structures, wherein each fingerprint map comprises a plurality of bit terms, wherein each bit term of the plurality of bits represents a different respective feature of a plurality of features of the chemical structure;

generating an inverted index for the collection of chemical structures, wherein the inverted index comprises a plurality of bit term posting lists, each bit term posting list corresponding to one of the bit terms, and wherein each bit term posting list is associated with all structures in the collection of chemical structures having a feature corresponding to the respective bit term of the bit term posting list, and wherein the inverted index further comprises a plurality of bit count posting lists, each bit count posting list corresponding to a number of bits that are set in each fingerprint map, and wherein each bit count posting list is associated with all structures in the collection of chemical structures having a fingerprint map with a number of bits that are set corresponding to the respective bit count of the bit count posting list;

receiving a request to search the inverted index for matching chemical structures, wherein the request specifies a query structure representing a chemical structure comprising one or more molecules;

obtaining a query fingerprint for the query structure, wherein the query fingerprint comprises a bit vector comprising bit terms representing which of the plurality of features are present in the query structure;

computing, based on the query fingerprint and a target score threshold, a minimum number of bits that must be present in respective fingerprints of candidate structures in the collection of chemical structures in order for a candidate structure to be considered a match for the query structure;

computing, based on the query fingerprint and the target score threshold, a maximum number of bits that can be present in respective fingerprints of candidate structures in order for a candidate structure to be considered a match for the query structure; and traversing the inverted index to identify candidate structures having fingerprints with a number of bits in between the minimum number of bits and the maximum number of bits, including rejecting as candidates any chemical structures that have fingerprints having fewer than the minimum number of bits or having greater than the maximum number of bits, comprising:

sorting a plurality of posting list identifiers according to a current structure identifier of each bit term posting list to generate a sorted list of posting list identifiers;

traversing the bit count posting lists to identify a current candidate structure identifier, wherein the current candidate structure identifier is associated with a current candidate structure having a fingerprint with greater than the minimum number of bits and less than the maximum number of bits;

designating a particular posting list identifier at a position in the sorted list corresponding to the minimum number of bits as a pivot term posting list;

designating the current structure identifier of the pivot term posting list as a current pivot structure identifier; and selecting a next bit term posting list to advance based on the current pivot structure identifier.

16. One or more non-transitory computer storage media storing instructions that when executed by one or more computers cause the one or more computers to perform operations comprising:

receiving a fingerprint map for each chemical structure of a collection of chemical structures, wherein each fingerprint map comprises a plurality of bit terms, wherein each bit term of the plurality of bits represents a different respective feature of a plurality of features of the chemical structure;

generating an inverted index for the collection of chemical structures, wherein the inverted index comprises a plurality of bit term posting lists, each bit term posting list corresponding to one of the bit terms, and wherein each bit term posting list is associated with all structures in the collection of chemical structures having a feature corresponding to the respective bit term of the bit term posting list, and wherein the inverted index further comprises a plurality of bit count posting lists, each bit count posting list corresponding to a number of bits that are set in each fingerprint map, and wherein each bit count posting list is associated with all structures in the collection of chemical structures having a fingerprint map with a number of bits that are set corresponding to the respective bit count of the bit count posting list;

receiving a request to search the inverted index for matching chemical structures, wherein the request specifies a query structure representing a chemical structure comprising one or more molecules;

obtaining a query fingerprint for the query structure, wherein the query fingerprint comprises a bit vector comprising bit terms representing which of the plurality of features are present in the query structure;

computing, based on the query fingerprint and a target score threshold, a minimum number of bits that must be present in respective fingerprints of candidate structures in the collection of chemical structures in order for a candidate structure to be considered a match for the query structure;

computing, based on the query fingerprint and the target score threshold, a maximum number of bits that can be present in respective fingerprints of candidate structures in order for a candidate structure to be considered a match for the query structure; and traversing the inverted index to identify candidate structures having fingerprints with a number of bits in between the minimum number of bits and the maximum number of bits, including rejecting as candidates any chemical structures that have fingerprints having fewer than the minimum number of bits or having greater than the maximum number of bits, comprising:

sorting a plurality of posting list identifiers according to a current structure identifier of each bit term posting list to generate a sorted list of posting list identifiers;

traversing the bit count posting lists to identify a current candidate structure identifier, wherein the current candidate structure identifier is associated with a current candidate structure having a fingerprint with greater than the minimum number of bits and less than the maximum number of bits;

designating a particular posting list identifier at a position in the sorted list corresponding to the minimum number of bits as a pivot term posting list;

designating the current structure identifier of the pivot term posting list as a current pivot structure identifier; and selecting a next bit term posting list to advance based on the current pivot structure identifier.

\* \* \* \* \*